US006364906B1

United States Patent
Baikoff et al.

(10) Patent No.: US 6,364,906 B1
(45) Date of Patent: Apr. 2, 2002

(54) INTRAOCULAR IMPLANT WITH FLEXIBLE OPTICAL PART AND SINGLE CIRCULAR LOOP

(75) Inventors: Georges Baikoff, Marseilles; Angel Ortuno, Choisy, both of (FR)

(73) Assignee: Corneal Laboratories, Paris (FR)

( * ) Notice: Subject to any disclaimer, the term of this patent is extended or adjusted under 35 U.S.C. 154(b) by 0 days.

(21) Appl. No.: 09/284,224

(22) PCT Filed: Oct. 10, 1997

(86) PCT No.: PCT/FR97/01807

§ 371 Date: Apr. 9, 1999

§ 102(e) Date: Apr. 9, 1999

(87) PCT Pub. No.: WO98/15239

PCT Pub. Date: Apr. 16, 1998

(30) Foreign Application Priority Data

Oct. 10, 1996 (FR) .............................................. 96 12360

(51) Int. Cl.[7] .................................................. A61F 2/16
(52) U.S. Cl. ....................... 623/6.4; 623/6.43; 623/6.46
(58) Field of Search ............................... 623/6.18, 6.19, 623/6.21, 6.22, 6.37–6.39, 6.43, 6.46, 6.47, 6.49, 6.5, 6.55, 6.11, 6.4–6.42, 6.48, 6.51, FOR 105

(56) References Cited

U.S. PATENT DOCUMENTS

| 4,494,254 A | 1/1985 | Lopez |
| 4,950,290 A | 8/1990 | Kamerling |

FOREIGN PATENT DOCUMENTS

| DE | 39 28 226 A | * | 5/1991 | ........ 623/FOR 105 |
| EP | 0 338 847 | | 4/1988 | |
| EP | 0 438 043 | | 7/1991 | |
| FR | 2 666 504 A | * | 3/1992 | ........ 623/FOR 105 |
| FR | 2 728 459 A1 | * | 6/1996 | ........ 623/FOR 105 |
| JP | 8-280721 A | * | 10/1996 | ........ 623/FOR 105 |
| WO | WO 94/28825 | | 12/1994 | |

* cited by examiner

Primary Examiner—David H. Willse
(74) Attorney, Agent, or Firm—Wolf, Greenfield & Sacks, P.C.

(57) ABSTRACT

The invention concerns an intraocular implant (10) comprising a substantially circular optical part (12) made of a first flexible material enabling it to be folded along a diameter and a haptic part (20). The haptic part (20) comprises a substantially ring-shaped body (22), substantially concentric and coplanar to the optical part, the body (22) has an opening, a first free end (26) and a second connecting end (28), the body (22) being made of material more rigid than the first, and a base (24) connecting in substantially radial manner the second end (28) of the haptic part body to a peripheral zone (16) of the optical part.

16 Claims, 4 Drawing Sheets

INTRAOCULAR IMPLANT WITH FLEXIBLE OPTICAL PART AND SINGLE CIRCULAR LOOP

The present invention relates to an intraocular implant for correction of aphakia, comprising a substantially circular optical part made of a first flexible material allowing it to be folded along a diameter, and a haptic part.

Intraocular implants constitute an optical system correcting the vision of the human eye which may, in a certain number of cases, replace corneal lenses or external corrector lenses. An intraocular implant is essentially composed of an optical part of generally circular or slightly ovalized shape which constitutes the optical corrector system proper, and by a haptic part which serves to position, fix and maintain the optical part in collect position inside the eye.

New operating techniques wake it possible to reduce the incision made in the eye. For example, in the case of the operation for cataract, the so-called phako-emulsification operating technique allows the ablation of the opaque lens by the introduction in the eye of an ultrasound probe presenting a system of irrigation/suction. By the combined action of the ultrasounds and of the flux of balanced saline solution, the lens is removed by emulsification.

This operating technique presents the advantage, particularly with respect to the prior techniques, of necessitating only all incision of reduced dimension in the cornea with the aid of a knife precalibrated at 2 to 4 mm to introduce in the eye the instruments necessary for this ablation. It will be understood that it is interesting to have implants available which can be introduced in the eye through the incision made for the phako-emulsification operation, i.e. an incision whose length is of the order of 3 to 4 mm.

This is why new, so-called flexible intraocular implants have been developed. They present all optical part made of a flexible material which makes it possible to fold the optical part before introduction of the implant in the eye through the incision, the optical part resuming its initial shape after it has been placed in the eye. At the present time, two major types of products are used for producing the flexible optical part. These products are usually designated under the generic name, on the one hand, of flexible acrylics such as pHEMA and, on the other hand, of polysiloxane gel. These materials present the required optical properties and are, moreover, biocompatible.

The ablation of the lens leads to the deformation by contraction of the capsular sac and consequently to its opacification. The deformation of the capsular sac may lead to the disappearance of the circular symmetry of the capsular sac and therefore to the disturbance of the vision of the eye by alteration of the axes of symmetry of the optical system constituted by the capsular sac and the intraocular implant.

The haptic part of the intraocular implants participates in the maintaining of the initial shape of the capsular sac, in particular its circular periphery.

The phenomenon of deformation of the capsular sac is non-negligible in the case of the haptic part being constituted by two identical loops diametrally opposite and symmetrical to each other with respect to the optical center as, in that case, the zones of contact between the loops and the inner wall of the capsular sac are two limited zones which must support entirely the pressure exerted by the two loops.

Moreover, it should be noted that the deformation by contraction of the capsular sac brings about a risk of partial tear of the zonular ligament which retains the capsular sac.

This is why it has been sought to develop implants with a circular haptic part which will be in contact with the inner wall of the capsular sac over relatively extended zones.

A first solution consists in using a haptic part constituted by two identical, rigid loops symmetrical to each other with respect to a diameter of the optical part. This configuration imposes loops with a small diameter in order to avoid their deforming too much and to prevent an offcentering of the implant in the capsular sac. Loops of great length are also necessary to try to obtain a zone of contact which is as wide as possible. In that case, the problem of the contraction of the capsular sac brings about the risk of an intersection, i.e. an overlapping between the free ends of the loops, which might lead to the perforation of the sac.

A second solution consists in using a single annular loop attached to the periphery of the optical part bit a connecting arm. In the implants made in this configuration, either the haptic part is rigid and a minimum folded implant width call no longer be obtained, which was possible with two symmetrical rigid loops, or the haptic part is flexible and pliable, but the maintaining of the implant in the eye by this flexible haptic part is insufficient for the intraocular implant to remain centered in the capsular sac without collapsing.

An object of the present invention is to produce an intraocular implant which allows both a fold along a diameter of the optical part so as to obtain a width of folded implant of the order of 3 or 4 mm and a maintenance of the implant in the eye by the haptic part which avoids the deformation of the capsular sac and the centering or displacement of the optical part of the implant.

In order to attain this object, the intraocular implant according to the invention comprises a substantially circular optical part made of a first flexible material enabling it to be folded along a diameter and a rigid haptic part, this implant being characterized in that the haptic part comprises a substantially ring-shaped body, substantially concentric and coplanar to the optical part, said body presenting an opening, a first free end and a second connecting end, said body being made of a second material more rigid than the first material, and a base connecting in substantially radial manner the second end of the body of the haptic part to a peripheral zone of the optical part, said base being connected to the periphery of the optical part over a sufficient length corresponding to an angle b less than 180 degrees in order to avoid a movement of torsion of the optical part with respect to the haptic part.

It will thus be understood that the optical part which is flexible may be folded along a diameter which effectively allows the introduction of the implant in the eye through an incision of small dimension. On the other hand, the haptic part being substantially circular and rigid, one has a good hold of the capsular sac. Finally, thanks to the structure of the base of the haptic part, a displacement of the optical part with respect to the haptic part is avoided.

In order to introduce the implant the folded optical part is firstly made to penetrate in the incision then the base of the haptic part and finally the annular body is entered by rotation of the implant about all axis parallel to its optical axis preferably while maintaining the annular body substantially coplanar to the optical part.

According to a preferred embodiment, the intraocular implant is characterized in that the haptic part comprises a substantially ring-shaped body substantially concentric and coplanar to the optical part, said body at least presenting an opening, a first free end and a second connecting end, said body being made of a second material more rigid than the first material, and a base connecting in substantially radial manner the second end of the body of the haptic part to a peripheral zone of the optical part said base being made of the same first material and presenting a lateral zone comprising a rigid armature (30a) made with the second material which extends said body at least as far as the periphery of the optical part.

According to an essential characteristic of this embodiment of the invention, to allow folding of the implant with the obtaining of a minimum folded implant width while allowing a centered hold of the implant in the eye, it is provided that said base presents a first lateral zone comprising a first rigid armature made with the second material which extends said body at least as far as the periphery of the optical part and a second lateral zone comprising a second rigid armature made with the second material, not extending over the whole length of this second lateral zone and adjacent the optical part, with the result that there exists at least one diameter of the optical part which extends in the base of the haptic part without cutting said armatures.

It will be understood that the haptic part of the implant according to the invention comprises a sufficiently rigid, annular body in one piece allowing an efficient hold of the implant in the eye by a minimum deformation of this body, and a maximum distribution of the pressure exerted by the haptic part on the wall of the capsular sac.

It will likewise be understood that, according to the preferred embodiment, the bi-material structure of the base of the haptic part of the implant makes it possible, on the one hand, to fold the implant along a diameter of the optical part traversing this base so as to obtain a minimum folded implant width and, on the other hand, a minimum offcentering thanks to the rigid armatures of the lateral zones of the base of the haptic part which prevent too great a deformation of the latter.

Thanks to the first radial armature of the base of the haptic part which extends the annular body as far as the periphery of the optical part, the optical part is maintained centred about the optical axis of the eye. The second rigid armature and the flexible central part of the base of the haptic part increase, on the one hand, the mechanical bending strength of the first armature connecting the optical part to the annular body and, on the other hand, the moment of inertia of the base of the haptic part. Such increase in the moment of inertia avoids any pivoting about the diameter of the optical part which extends in the flexible central part of the base of the haptic part. In effect, such a pivoting would offset the optical axis of the implant with respect to the optical axis of the eye as they would no longer be parallel to one another and this would considerably spoil the optical correction contributed by the implant.

It should be noted that the implant according to the invention is not forcibly intended to be placed solely in the capsular sac; it may for example also be positioned in the posterior chamber of the eye, by bearing in the irido-ciliary groove (sulcus).

The invention will be more readily understood and the secondary characteristics and their advantages will appear in the course of the description of preferred embodiments given here in below by way of example.

It is understood that the description and the drawings are given only by way of descriptive and non-limiting example.

Reference will be made to the accompanying drawings, in which.

Figure 1:
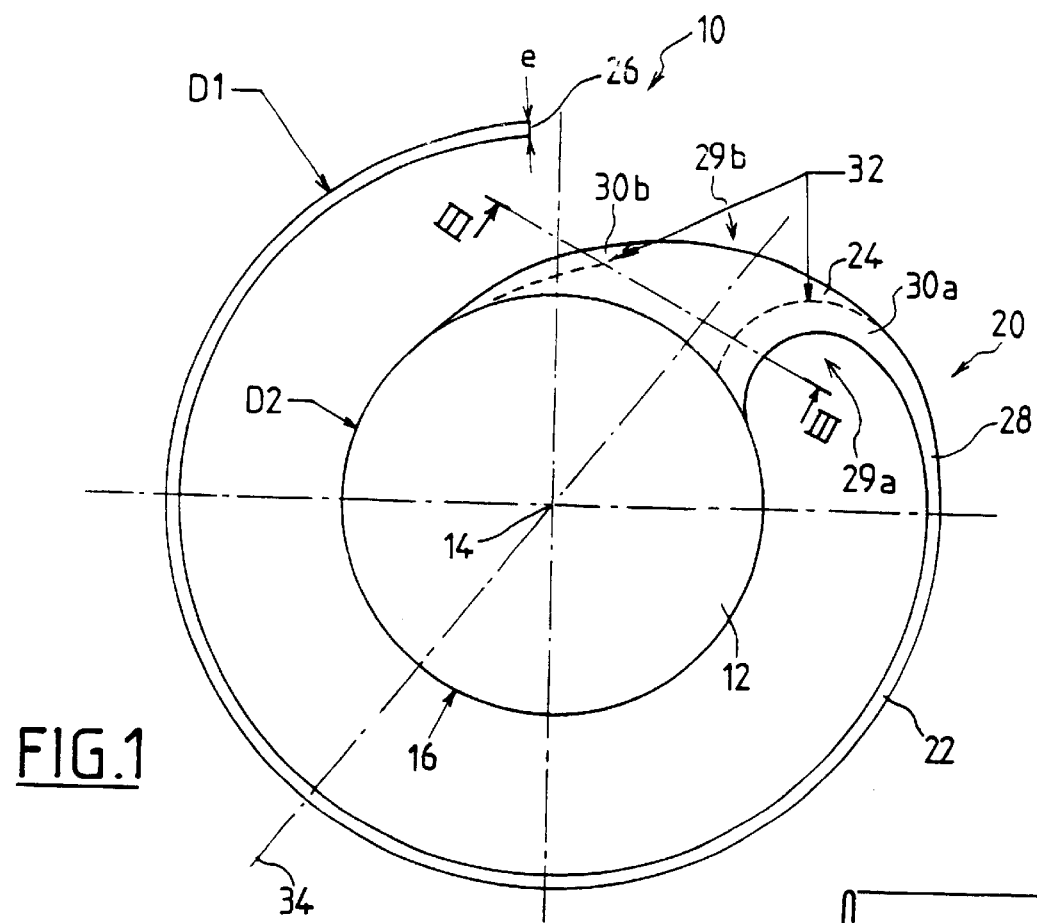
FIG. 1 is a front view of an intraocular implant according to a preferred embodiment of the invention, presenting an annular haptic part made of two materials.
Figure 5:
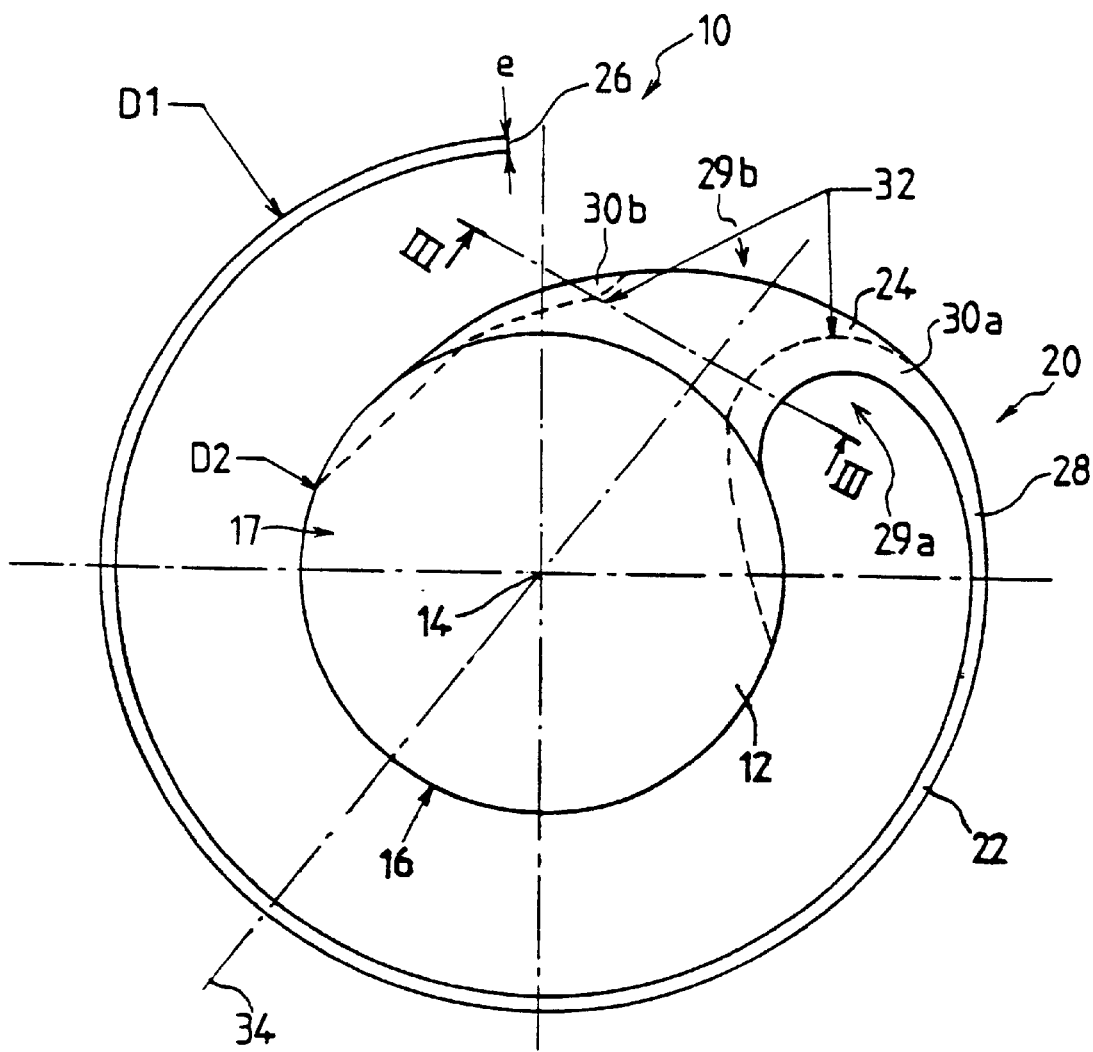

FIG. 5 presents a first variant embodiment of the implant of FIG. 1.

Figure 6:
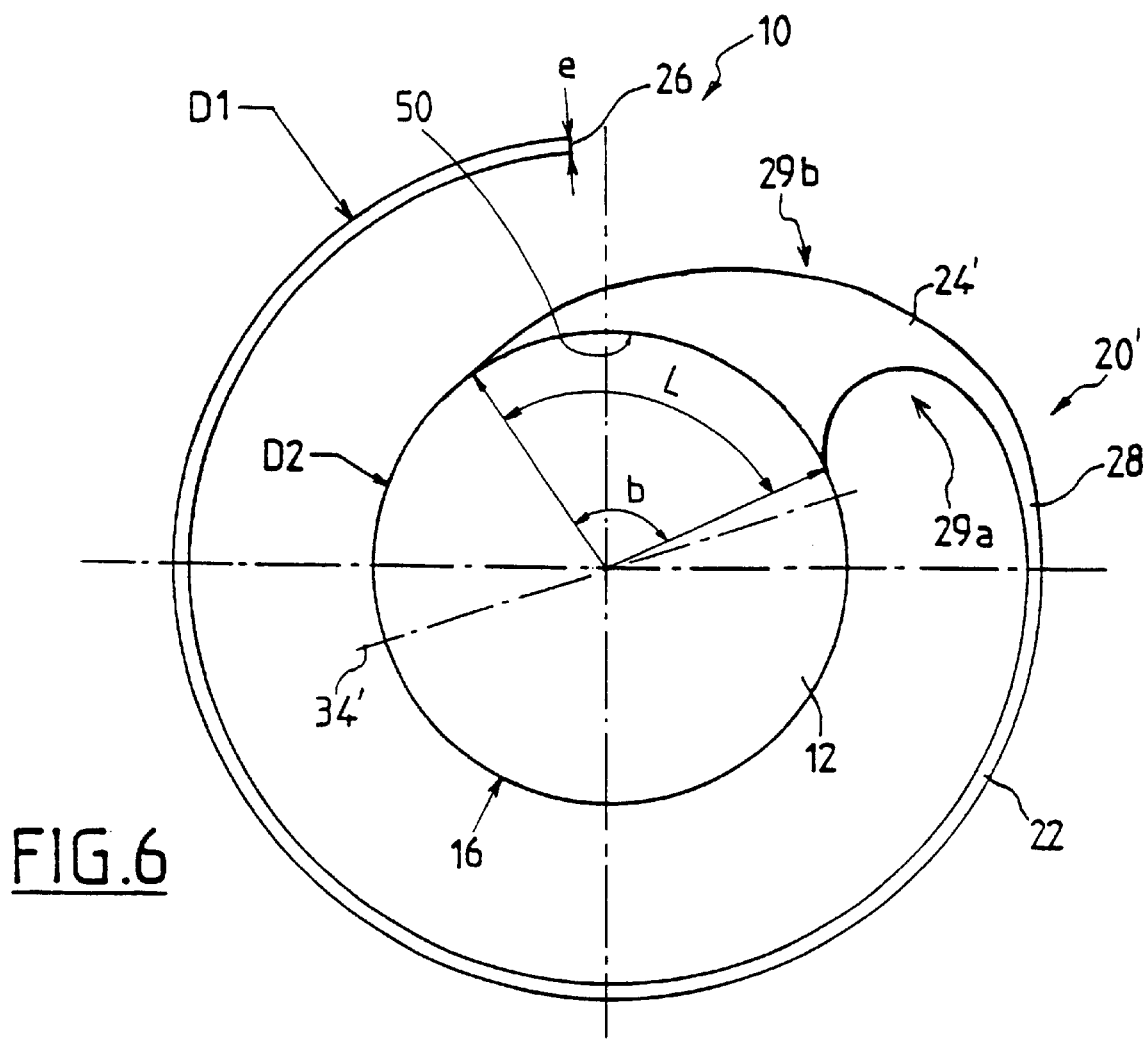

FIG. 6 illustrates a second embodiment of the invention, and

Figure 7:
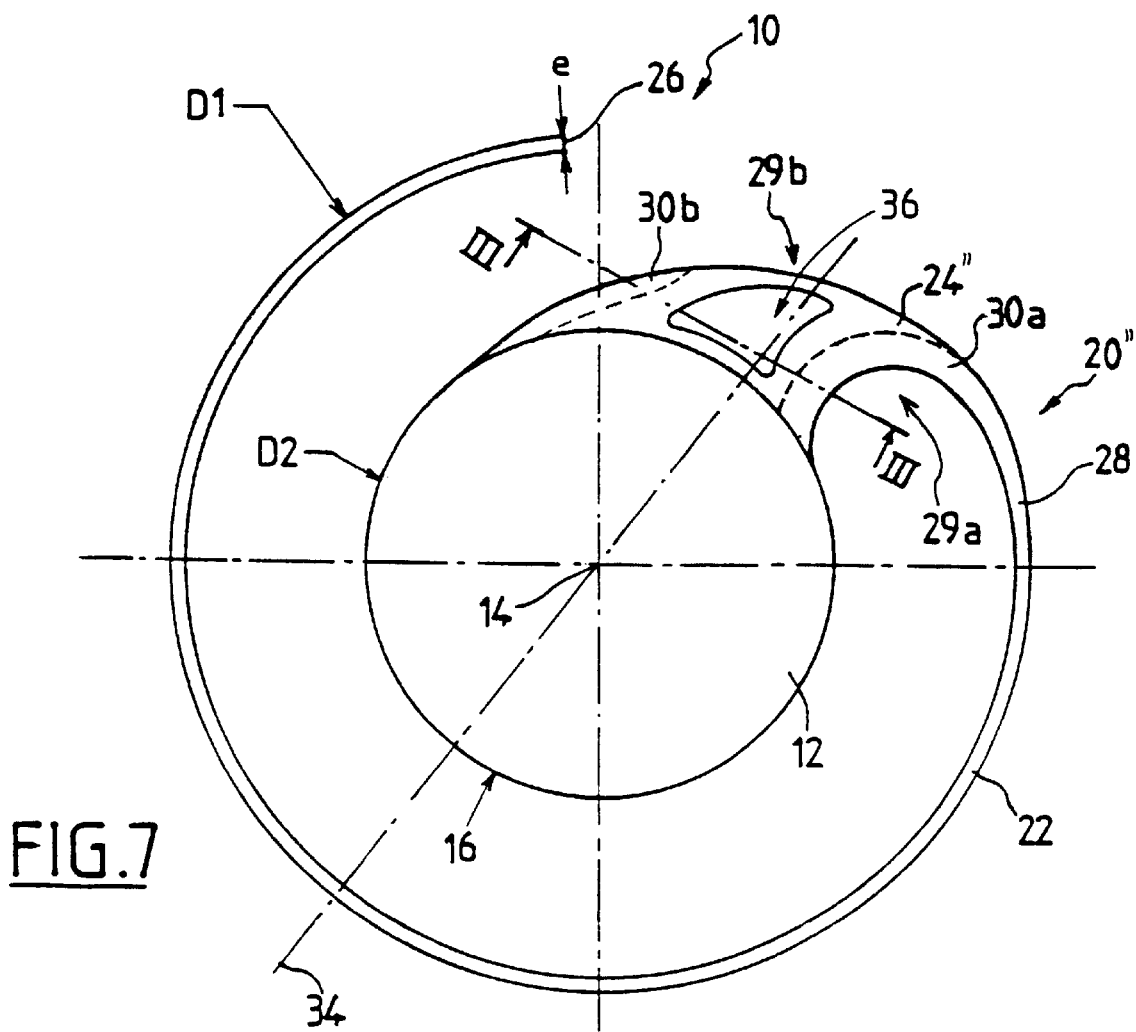

FIG. 7 represents a second variant embodiment of the implant of FIG. 1.

According to a preferred embodiment shown in FIG. 1, the intraocular implant 10 comprises an optical part 12 in the form of a lens which may be biconvex presenting an optical center 14 and a convex periphery 16. The haptic part 20 of the intraocular implant may be split tip into an annular body 22 and a base 24 connecting the optical part 12 to the body 22 of the haptic part 20.

The optical part 12 of the ocular implant is made of a first flexible material allowing this optical part to be folded, for example a copolymer based on pHEMA or a material comprising a hydrophilic acrylate or silicone gel. The body 22 of the haptic part 20 forms an open ring made of a second material which is rigid, such as PMMA. The annular body 22 of the haptic part 20 extends from a free end 26 tip to a connecting end 28 which will be connected to the optical part 12, the arc of circle included between these two ends preferably forming an angle at the center at least substantially equal to 270°. It is provided that the thickness e of the annular body 22 be substantially constant preferably of the order of 0.20 mm, the diameter D1 of this annular body 22 preferably being of the order of 10 to 11 mm.

The diameter D2 of the optical part 12 is conventionally of the order of 5 to 6 mm.

The base 24 of the haptic part 20 will now be described in relation with FIG. 1 This base 24 makes it possible to connect the optical part 12 substantially radially to the annular body 22 of the haptic part 20. This base 24 is essentially constituted by the flexible material previously cited and presents, in its two lateral zones 29a and 29b extending from the periphery 16 of the optical part in the direction of the annular body 22 of the haptic part 20, two rigid armatures 30a and 30b constituted by the second material, the limits between the first and the second materials being represented by dotted lines 32 in FIG. 1.

One sole rigid, radial armature 30a can be imagined, extending the annular body 22 radially as far as the periphery 16 of the optical part.

The first rigid armature 30a extends the optical part 12 to the annular body 22, extending continuously and radially from the end of the first lateral zone 29a of the base 24 of the haptic part which is adjacent the periphery 16 of the optical part, on the side closest to the connecting end 28 of the annular body 22, up to this connecting end 28. The second rigid armature 30b extends on the second lateral zone 29b of the base 24 of the haptic part 20 from the periphery 16 of the optical part 12 as far as about the middle of this lateral zone, without being joined to the second material whether it be with the first armature 30a or with the connecting end 28 of the annular body 22.

In this way, the edge of the base 24 of the haptic part 20 is not entirely constituted by the second rigid material and there exists at least one diameter of the optical part 12 which extends in the base 24 of the haptic part 20 without intersecting the second material is it encounters only the first material, The implant may therefore be folded along a folding axis 34 passing through said diameter of the optical part and the base of the haptic part without cutting one of the rigid armatures.

The base 24 presents a general radial direction so as to join the optical part to the annular body 22 of the haptic part.

The rigid armatures 30a and 30b preferably present a minimum thickness and width of 0.1 mm; the zone of the base 24 of the haptic part joined to the optical part 12 presents a width which may vary between 1 mm and the diameter D2 of the optical part and a thickness between 0.15 and 0.4 mm.

The outer contour of the lateral zones of the base 24 of the haptic part 20 is preferably curved. The radius of curvature of the outer contour of the first lateral zone 29a is chosen and positioned so as preferably to form a fillet or groove at the level of the zone of joining between the peripheral zone 16 of the optical part and the base 24 of the haptic part. The radius of curvature of the outer contour of the second lateral zone 29b is chosen and positioned so that this contour extends the outer contour of the optical part 12 substantially tangentially The connection between the base 24 of the haptic part 20 and the connecting end 28 of the annular body 22 is also perferably effected in substantially tangential manner.

This rounded shape of the ease 24 of the haptic part allows a better distribution off the stresses on this zone, hence a less localized deformation and a reduced risk of offcentering of the implant in the eye.

Rigid armatures 30a and 30b presenting a substantially constant width whose profile follows the shape of the outer contour of the lateral zones of the base 24 of the haptic part 20, will be privileged.

The distribution of the first aid of the second material respectively flexible and rigid, in the transverse section of the base 24 of the haptic part at the level of a zone comprising the two armatures 30a and 30b will now be described, in relation with FIGS. 3 and 4. In both cases, one finds that the second rigid material constituting the armatures 30a and 30b opens outside the base 24 of the haptic part 20 in the direction of the lateral faces of the base 24.

Figure 3:
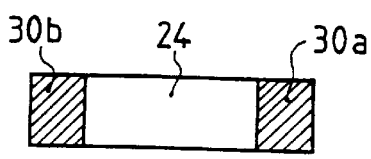
FIG. 3 is a transverse section in the direction III—III of FIG. 1 and represents, on a larger scale, the distribution of the different materials in the section of the base of the haptic part.
Figure 4:
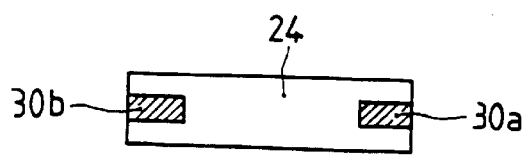
FIG. 4 is a view identical to that of FIG. 3 corresponding to a variant embodiment.
Figure 2:
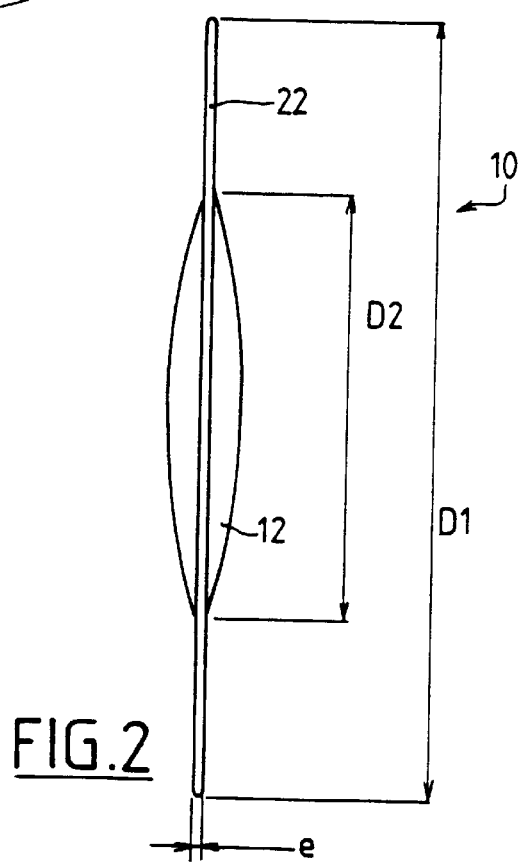
FIG. 2 is a side view of the intraocular implant shown in FIG. 1.

In the case of FIG. 3, the second rigid material fills all the thickness of the base 24 but it is possible to provide, as in the case of FIG. 4, that this second material fills only a part of the thickness of the parts of the lateral zones 29a and 29b of the base 24 comprising the armatures 30a and 30b, preferably a median zone of the thickness surrounded on either side by the first flexible material which constitutes the essential part of the base 24 of the haptic part 20.

The periphery 16 of the optical part 12 is connected to the base 24 of the haptic part 20 along an arc of circle with angle at the centre at least substantially equal to 90°.

The variant embodiment shown in FIG 5 consists in extending the armatures 30a and 30b in the peripheral zone 17 of the optical part 12 over a length of the periphery which may go up to about 3 mm.

A process of manufacture allowing the intraocular implant 10 according to the invention to be produced, will now be described. A plate made of the second rigid material is used, whose dimensions are sufficient to include the whole implant, and a recess corresponding, to the optical part 12 and to the zone of the base 24 of the haptic part 20 which will be solely constituted by the first flexible material, is created by machining this plate. Then the optical part 12 and the base 24 of the haptic part is moulded in a moulding device shaped to the desired geometry. For this moulding step, reference may for example be made to French Patent Applications Nos. 94 12274 and 94 12275 corresponding to PCT Application No. PCT/FR95/01344. During this hot moulding step, an interpenetration of the molecular networks of the first and second macromolecular materials will be effected so as to obtain a very strong bond between flexible and rigid materials. In this way, a connection is obtained between the second material constituting the rigid armatures and the first material which is located, on the one hand, in the zone of the periphery of the optical part adjacent these armatures and, on the other hand, in the lateral zones of the base of the haptic part.

To finish production of this intraocular implant, the first material will be machined, if this is possible and necessary, so as to obtain the optical characteristics of the optical part 12 which are in accordance with those of the implant that it is desired to make, and the precise machining is effected of the second material, i.e. of the base 24 and of the annular body 22 of the haptic part 20.

Possible subsequent treatments may be carried out on this ocular implant in accordance with the treatments usually carried out on this type of implant with flexible optical part.

Similarly, suitable treatments may be carried out on the haptic part of the implant in order to give it specific properties.

Referring now to FIG. 6. a second embodiment of the implant will be described. This implant still comprises a circular optical part 12 made of a flexible material and a haptic part 20' constituted by an annular body 22 and a base 24' connecting the optical part to the body 22.

According to this embodiment, the annular body 22 is identical to the body 22 of FIGS. 1 and 5, only base 24' being, modified.

More precisely, the base 24' is entirely made with the same material as the annular body 22. It may be PMMA.

The base is connected to the periphery 16 of the optical part by any suitable means compatible with the materials constituting the optical part and the haptic part. The connection may preferably, but not exclusively, be obtained by interpenetration of networks between the two materials.

In order to ensure a sufficient mechanical connection between the two parts of the implant, the length L of the zone of contact 50 must be sufficient. The angle at the centre b corresponding to this connection is preferably greater than 45 degrees. However, it will be understood that this angle b must be strictly less than 180 degrees, in order to leave "free" a folding diameter of the optical part 12. FIG. 6 shows a possible folding diameter 34'. Other folding diameters might, of course, be used, on condition that it does not "cult" the zone of contact 50.

The length L of the connection between the periphery of the optical part and the beginning of the base 24' of the haptic part also makes it possible to avoid a torsional moment that can develop at the level of the base which might result in the plane of the optical part and the plane of the haptic part no longer merging. In addition, the relatively solid and therefore rigid nature of the base 24' of the haptic part ensures correct centering of the optical part with respect to the annular body 22 of the haptic part.

Variants of the second embodiment may be envisaged with a base made entirely with the same flexible material or first material as the optical part 12 or a base comprising certain zones made with the first material, the other zones being made with the second material constituting the annular body. Depending on the distribution between flexible material and rigid material, it may be envisaged that the folding axis traverses the base if this axis does not encounter the rigid material.

FIG. 7 will now be described which illustrates a second variant of the first embodiment (FIG. 1). The implant of FIG. 7 is identical to that of FIG. 1 except concerning, the base. A flexible optical part 12 and a haptic part 20" constituted by a rigid annular body 22 and a base 24" connecting the optical part 12 to the annular body 22, are found again.

The base 24" comprises the two rigid armatures 30a and 30b on either side of the central zone made in the first material, said zone presenting a recess 36. This recess 36 is made spaced apart from the rigid armatures and does not cause a substantial fragilization of the base 24", with the result that the optical part 12 and the annular body 22 remain substantially coplanar.

Thanks to the presence of this recess, when the implant has been placed in position in the eye, the portions of the anterior and posterior walls of the capsular sac which are opposite the recess, oil either side of the base 24", will be able to adhere to each other and merge together. In this way, the stability of the position of the intraocular implant in the capsular sac is reinforced any offcentering or rotation of the implant with respect to the capsular sac is prevented, with the result that the optical axis of the optical part 12 remains aligned with the optical axis of the eyeball. Moreover, since this recess 36 serves as point of adhesion between the implant and the capsular sac, the retain forces exerted by the annular body 22 on the capsular sac may be less great.

The variant embodiment consisting in providing a recess 36 in the central zone of the base may be made in sill the other cases described hereinbefore, i.e. with a base 24 presenting armatures (FIGS. 1 and 5), a base 24' without armatures (FIG. 6) and whatever the shape or whatever the material constituting this base.

Another important characteristic of the present invention resides in the fact that the base presents a width which decreases regularly from the periphery of the optical part (width L) until it reaches the connecting, end 28 of the annular body 22 (width e).

What is claimed is:

1. An intraocular implant comprising:
    a substantially circular optical part made of a first flexible material enabling it to be folded along a diameter; and
    a haptic part comprising:
        a substantially ring-shaped body, substantially concentric to the optical part; and
        a base;
        wherein said ring-shaped body comprises a first free end and a second connecting end;
        wherein said ring-shaped body is made of a second material more rigid than the first material; and
        wherein said base connects in substantially radial manner the second connecting end to a peripheral zone of the optical part over a sufficient length corresponding to an angle at a center of the optical part less than 180 degrees and more than 45 degrees to avoid a movement of torsion of the optical part with respect to the haptic part.

2. The intraocular implant according to claim 1, wherein said base is made of the first material and has a lateral zone comprising a rigid armature made with the second material which extends within said body at least up to the peripheral zone.

3. The intraocular implant according to claim 2, wherein said base further comprises a second lateral zone comprising a second rigid armature made of the second material, not extending over the whole length of the second lateral zone and adjacent the optical part so that there is at least one diameter of the optical part not intersecting said armatures as it extends through the base of said haptic part.

4. The intraocular implant according to claim 3, wherein an outer contour of said lateral zones of the base of the haptic part is curved.

5. The intraocular implant according to claim 3 wherein an outer contour of said lateral zone of the base of the haptic part is shaped to form, at the level of the zone of joinder between the peripheral zone of the optical part and the base of the haptic part, a groove for the first lateral zone and a tangential extension of an outer contour of the optical part for the second lateral zone.

6. The intraocular implant according to claim 3 wherein said rigid armatures have a substantially constant width which follows the shape of an outer contour of said lateral zones.

7. The intraocular implant according to claim 3 wherein said rigid armatures open out on lateral faces of the base.

8. The intraocular implant according to claim 3 wherein said second material fills at least a part of a thickness of parts of the lateral zones comprising the rigid armatures.

9. The intraocular implant according to claim 1, wherein said ring-shaped body covers an arc of at least 270°.

10. The intraocular implant according to claim 3 wherein at least one of said rigid armatures extends up to the peripheral zone of the optical part.

11. The intraocular implant according to claim 1, wherein said second material is PMMA.

12. The intraocular implant according to claim 1, wherein said first material includes a hydrophilic acrylate.

13. The intraocular implant according to claim 1, wherein said first material is silicone gel.

14. The intraocular implant according to claim 1, wherein said base further comprises a recess adapted to allow merging of a portion of an anterior wall and a posterior wall of a capsular sac of an eye in which said implant is intended to be housed.

15. The intraocular implant according to claim 1, wherein the haptic part and the optical part form a one-piece intraocular implant.

16. An intraocular implant comprising:
    a substantially circular optical part having a substantially circular periphery, an optical axis and an optical plane perpendicular to said optical axis, and being made of a first flexible material able to be folded along a diameter; and
    a haptic part, the haptic part and the optical part being formed of one piece, the haptic part comprising:
        a substantially annular body substantially concentric to said optical part and substantially parallel to said optical plane, said body comprising a first free end, and a second connecting end, said body being made of a second material more rigid than said first flexible material; and
        a single base having a substantially radial direction with respect to said optical part, a first end of the base being connected to said periphery of said optical part, and a second end of the base being connected to said second connecting end of the annular body of the haptic part,
        said base being connected to the periphery of said optical part over a continuous length corresponding to an angle at the center of the optical part of less than 180° and more than 45° to avoid a torsional movement of the optical part with respect to the haptic part,
        said annular body being connected to said optical part only by said single base.

* * * * *